(12) United States Patent
Mason

(10) Patent No.: US 6,253,774 B1
(45) Date of Patent: Jul. 3, 2001

(54) COMPACT DENTAL FLOSSING TOOL

(76) Inventor: Robert F. Mason, 5800 South St., #140, Lakewood, CA (US) 90713

( * ) Notice: Subject to any disclaimer, the term of this patent is extended or adjusted under 35 U.S.C. 154(b) by 0 days.

(21) Appl. No.: 09/472,588

(22) Filed: Dec. 27, 1999

(51) Int. Cl.[7] .................................................. A61C 15/00
(52) U.S. Cl. ............................................................. 132/325
(58) Field of Search .................................. 132/324, 325, 132/326, 327, 328, 332; 242/129.8, 137, 138, 146; 206/63.5, 368, 63.3, 409

(56) References Cited

U.S. PATENT DOCUMENTS

| | | | |
|---|---|---|---|
| 3,890,986 | * 6/1975 | Gerlich | 132/324 |
| 4,821,752 | * 4/1989 | Widlak | 132/324 |
| 4,934,389 | * 6/1990 | Pettiford | 132/324 |
| 5,183,065 | * 2/1993 | Mason | 132/324 |
| 5,251,651 | * 10/1993 | Mason | 132/324 |
| 5,544,831 | * 8/1996 | Van Netta | 242/127 |
| 5,566,872 | * 10/1996 | Dolan et al. | 132/325 |
| 5,573,022 | * 11/1996 | Winters | 132/325 |
| 5,607,050 | * 3/1997 | Dolan et al. | 132/325 |

* cited by examiner

*Primary Examiner*—Gene Mancene
*Assistant Examiner*—Eduardo C. Robert
(74) *Attorney, Agent, or Firm*—Robert M. Sperry

(57) ABSTRACT

An improved dental flossing container comprising a generally cup-shaped housing, a spool of dental floss located within the housing, the housing being formed with an opening for allowing floss from the spool to exit, resilient device closing the open end of the housing, brake device to clamp the floss and, when not depressed, allowing the spool to move forward to engage device to lock the floss form moving, and rear cap device selectably positionable to allow or prevent moisture from entering the housing, and a device located within the housing causing the floss to pass forward through the open end of the housing.

28 Claims, 3 Drawing Sheets

COMPACT DENTAL FLOSSING TOOL

BACKGROUND

1. Field of Invention

This invention relates to dental flossing tools and is particularly directed to dental flossing tools which are compact, easy to use and which can serve as the floss containers for other flossing tools.

1. Prior Art

As is well known, the flossing of teeth is a very important part of proper dental hygiene. Unfortunately, many people fail to follow this procedure or perform the flossing operation incorrectly or inefficiently. Numerous types of dental flossing tools have been proposed heretofore to overcome these problems. Prior art dental flossing tools are often relatively bulky and, therefore, are awkward and cumbersome to use. Also, many prior art can hold only a small supply of floss. With this tool, the dental floss is drawn from the spool in an endwise direction. Dental flossing material is usually waxed and, hence, tends to adhere to the spool, which makes it pull the spool forward, as the floss is drawn off of the spool, causing the spool to jam against the forward end of the housing. This produces friction which slows or actually stops the spool form turning. Furthermore, many prior art flossing tools cannot prevent moisture from entering the housing and, hence, are subject to contamination by accumulated moisture. Thus, none of the prior art dental flossing tools has been entirely satisfactory.

BRIEF SUMMARY AND OBJECTS OF THE INVENTION

These disadvantages of prior art dental flossing tools are overcome with the present invention and an improved dental flossing container is provided which is compact and easy to use, yet holds a full spool of dental floss, and which clamps the floss as it exits the tool to lock the floss against movement and to prevent moisture from entering the housing and means for ventilating the housing to allow moisture, if any, contained in the housing to evaporate.

The advantages of the present invention are preferably attained by providing an improved dental flossing container comprising a generally tubular housing having an open end, a spool of dental floss located within said housing, a resilient lid covering the open end of said housing and formed with an opening for allowing floss from said spool to exit, yet serving to clamp said floss and to lock said floss form moving and to prevent moisture from entering said housing, rear cap means for ventilating said housing when the rear cap is open, and means located within said housing causing the floss to pass forward through said lid.

Accordingly, it is an object of the present invention to provide an improved dental flossing container.

Another object of the present invention is to provide an improved dental flossing container having an internal storage area for flossing material.

A further object of the present invention is to provide an improved dental flossing container having a tip where flossing material exits the container and having means located adjacent the tip for preventing moisture from passing through the tip to the interior of the container.

Another object of the present invention is to provide an improved dental flossing container having an internal storage area for dental flossing material, together with means for causing the floss to pass forward through the tip of the tool.

A specific object of the present invention is to provide an improved dental flossing container comprising a generally cup-shaped housing, a spool of dental floss located within said housing, said housing being formed with an opening for allowing floss from said spool to exit, resilient means closing said open end of said housing, brake means serving to clamp said floss and, when not depressed, allowing said spool to move forward to engage means to lock said floss form moving, and rear cap means selectably positionable to allow or prevent moisture from entering said housing, and means located within said housing causing the floss to pass forward through said opening of said housing.

These and other objects and features of the present invention will be apparent from the following detailed description, taken with reference to the figures of the accompanying drawing.

DETAILED DESCRIPTION OF THE INVENTION

Figures 1, 2:
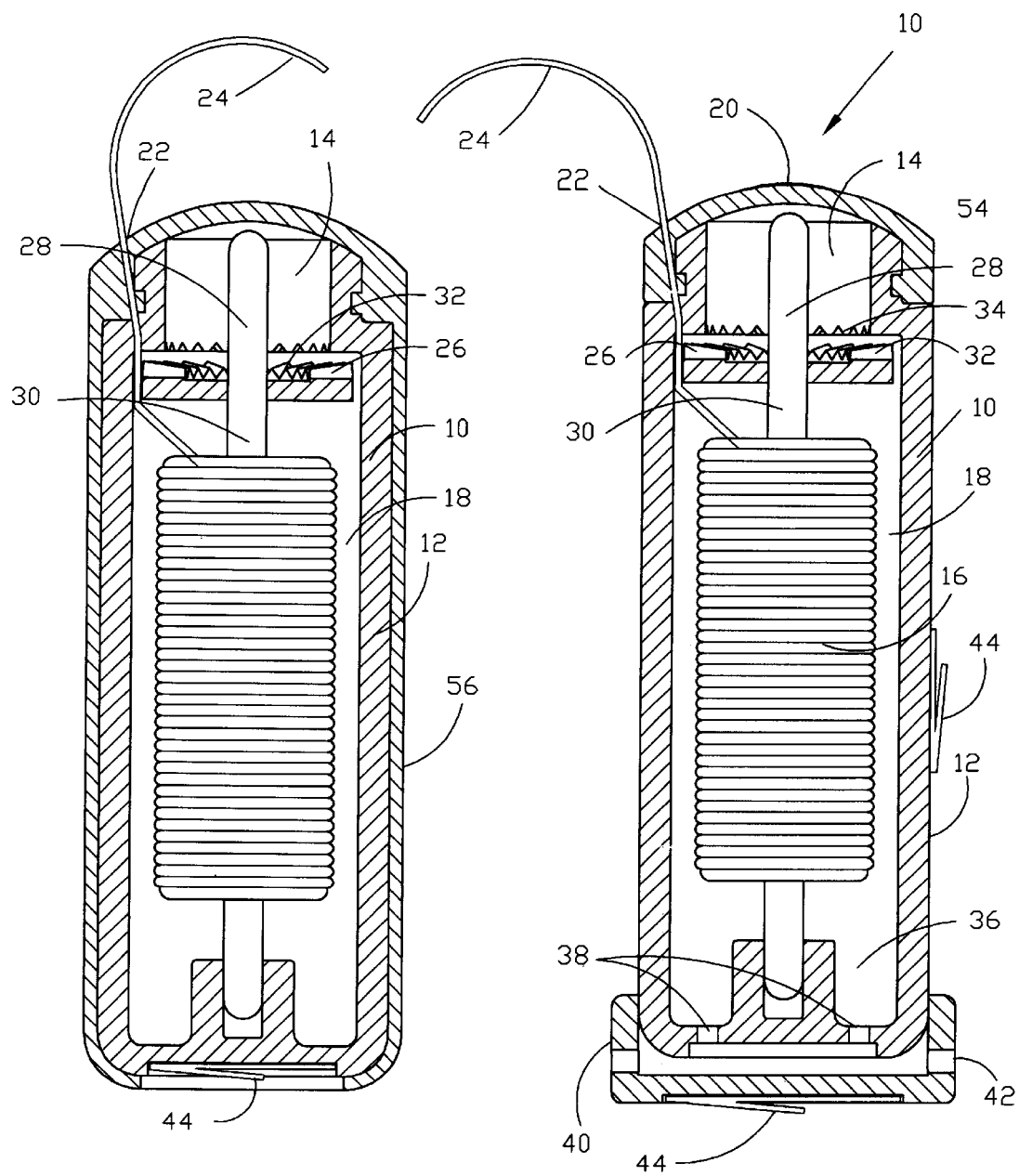
FIG. 1 is a longitudinal section through a dental flossing tool embodying the present invention.
FIG. 2 is a view, similar to that of FIG. 1, showing an alternative lid which encloses the entire tool.
Figure 4:
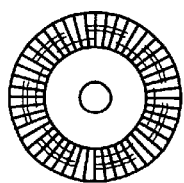
FIG. 4 is a plan view of the floss spool of FIG. 3.
Figure 3:
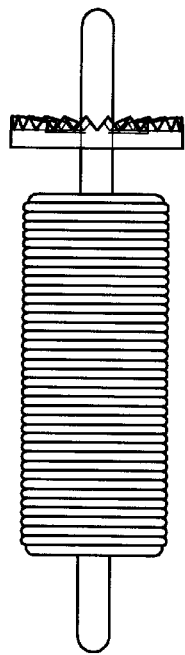
FIG. 3 is a side view of the floss spool for use with the dental flossing tool of FIG. 1.

In that form of the present invention chosen for purposes of illustration in FIG. 1, a dental flossing container, indicated generally at 10, is shown comprising a generally cylindrical, hollow housing 12 having an open forward end portion 14 to permit a spool 16 of dental flossing material to be loaded into or removed from a storage area 18 within the housing 12. A lid 20 formed of resilient material, such as rubber serves to close the open end 14 of the housing 12 and is formed with a suitable aperture 22 to allow a strand 24 of the flossing material to exit the dental flossing container 10. Aperture 22 is sufficiently large to allow passage therethrough of the floss strand 24. However, because the lid 20 is formed of resilient material, the sides of the aperture 22 grip the floss strand 24 to prevent moisture from being wicked into the interior of the housing 12. A brake member 26 is provided adjacent of end 28 of the shaft 30 of the floss spool 16 and carries a plurality of teeth 32 which are engageable with teeth 34 formed on the interior of the housing 12. Adjacent its lower end 36, the housing 12 is formed with a plurality of openings 38 and a rear cap 40 is frictionally slidably mounted on end 36 of the housing 12 and is provided with openings 42 which are positionable, as seen in FIG. 1, to allow ventilating air to enter the housing 12 and is movable to a closed position in which the openings 42 become closed to prevent undesired air from entering the housing 12. If desired, a floss cutting device, such as blade 44 may be provided on the bottom or outer surface of the rear venting cap 40. Alternatively, as seen in FIG. 1, the blade 44 may be mounted on the outside of the rear end of housing 12.

In use, the lid 20 is removed and the floss spool 16 is inserted into the housing 12 with the floss strand 24 being led to exit through aperture 22 of the lid 20. The lid 20 is then placed on the housing 12 and the dental floss container is ready for use as a flossing tool. To perform the flossing operation, the user grasps the container 10 in one hand, grasps the exposed end of the floss strand 24 with the other hand. Note that, until the user presses the lid 20 inwardly, pulling on the floss strand 24 tends to pull the floss spool 16 forward, causing the spool 16 to bear against brake member 26 and causing teeth 32 of the brake member 26 to engage teeth 34 of lid 20, which serves to lock the floss spool 16 against rotation and to prevent additional floss from being withdrawn from this floss spool 16. However, when the user presses inwardly on lid 20, this causes teeth 34 of the cap to disengage from teeth 32 of the brake member 26, which allows free rotation of the floss spool 16 to enable the user to draw off a desired length of the floss strand 24 from floss spool 16. Releasing the lid 20 causes the teeth 34 of the cap to reengage with teeth 32 of the brake member 26 to prevent further rotation of the floss spool 16. Thereafter, the user proceeds to perform the flossing operation in the usual manner, after which, the user draws the floss strand 24 against the cutter blade 44 to sever the used floss. If desired, the user can then pull rear cap 40 downwardly to open the holes 42 of the rear cap 40 to allow air to enter holes 38 of the housing 12 to ventilate the interior of the housing 12. The housing maybe unopenable.

FIG. 2 shows an alternative form of the dental flossing container 10 in which lid 20 is formed with a skirt 56 which encircles the housing 12 and extends substantially the entire length of the housing 12.

Figure 5:
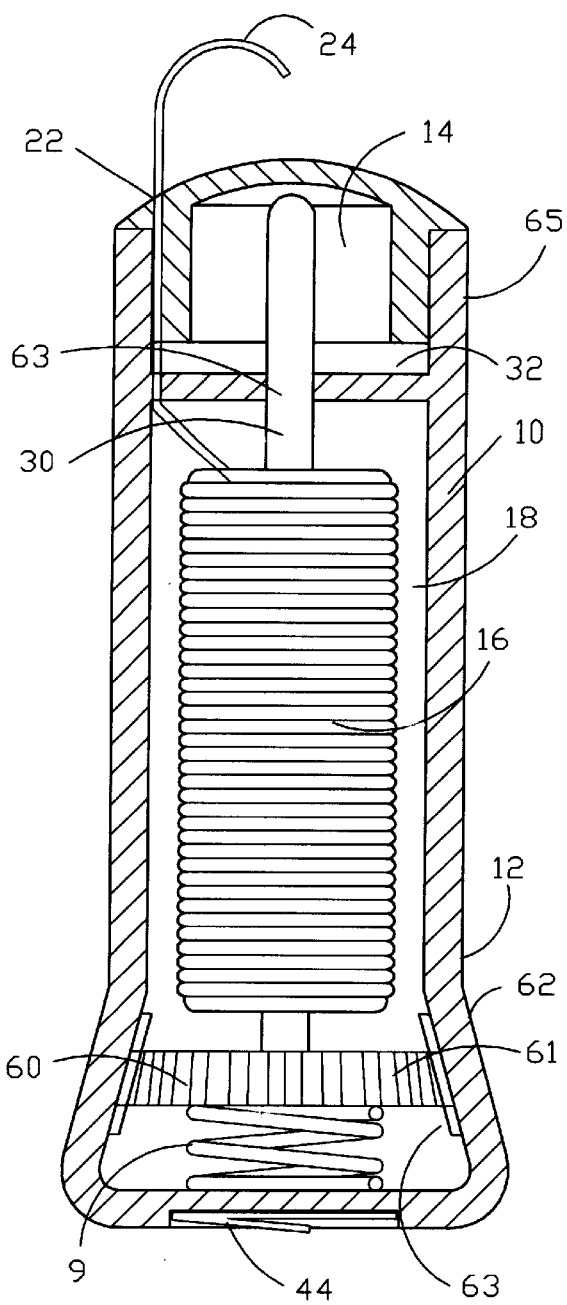
FIG. 5 is a view, similar to that of FIG. 1, showing an alternative form of the dental flossing tool of FIG. 1.

FIG. 5 shows another means of stopping rotation of the floss spool 16. In this form of the present invention, shaft 30 has a disc 60 at the bottom of housing 12 with a web 63 supporting the shaft 30 at the forward end 65 of container 10. When the floss strand 24 is pulled, the floss spool 16 is pulled forward, causing the disc 60 to engage the tapered wall 62 of housing 12 to cause frictional stopping of the floss spool 16. Also, if desired, disc 60 can have vertical teeth 61 to mesh with vertical lines 63 on the tapered wall 62 of housing 12 to further lock the floss spool 16 against rotation. A spring 9 can assist in pushing the floss spool 16 forward into the locking position. This form of the dental flossing container 10 is loaded from the bottom and the floss exits by passing between plug 20 and the interior of the housing 12.

Figure 6:
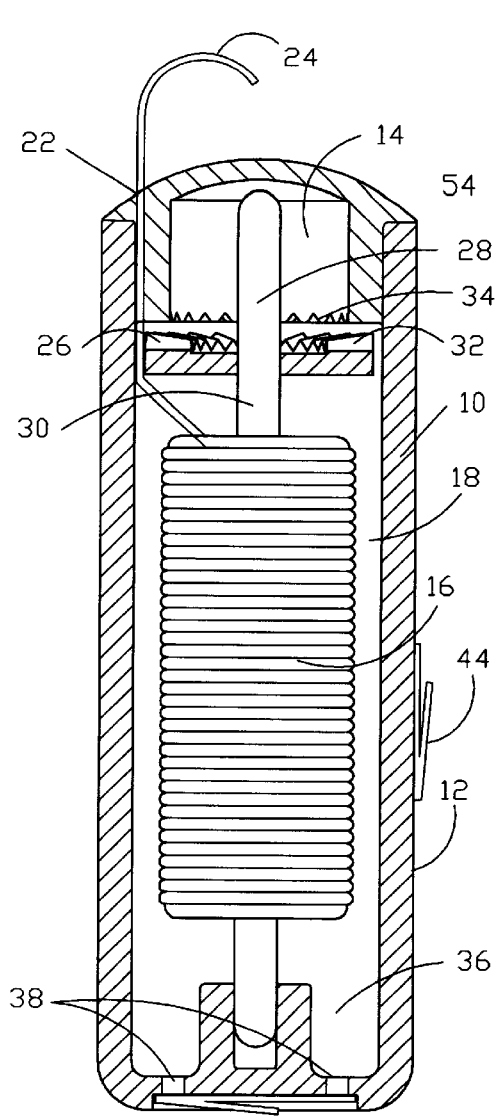
FIG. 6 is a view, similar to that of FIG. 1, showing another alternative form of the dental flossing tool of FIG. 1.

FIG. 6 is a view, similar to that of FIG. 1, showing an alternative form of the forward end portion 14. The cap 20 now forms a plug, allowing the floss strand 24 to pass between the plug 20 and the interior of the housing 12, compressing the floss strand 24 and, at the same time, sealing the forward end portion 14 of the dental flossing container 10.

Figure 7:
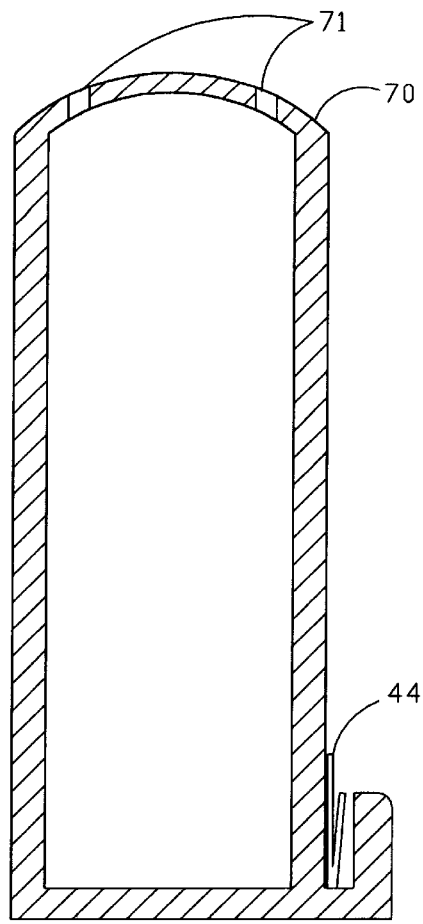
FIG. 7 is a longitudinal view of an alternative form of the dental flossing tool cover of FIG. 1 having the cut-off formed thereon.

FIG. 7 shows a cover 70 having cutter 44 as a part thereof and can have vent holes 71 to keep the forward end portion 14 of the housing 12 dry and free from germs.

Figure 8A:
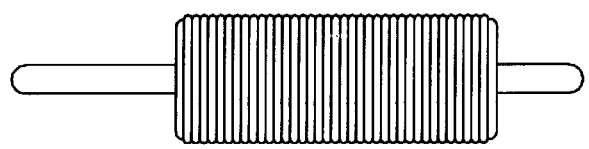
FIG. 8 A and B are detail views showing two alternative forms of the floss spool of the dental flossing tool of FIG. 1.
Figure 8B:
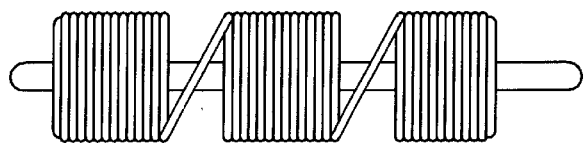

FIG. 8 shows two different styles of the floss spool 16. The form of FIG. 8a is wound like a spool of thread. He form of FIG. 8b is wound in more than one continuous segment.

Obviously, numerous other variations and modifications can, obviously, be made without departing from the spirit of the present invention. Therefore, it should be clearly understood that the forms of the present invention described above and shown in the accompanying drawing are illustrative only and are not intended to limit the scope of the present invention.

What is claimed is:

1. A dental floss container comprising:
   a cylindrical housing having open end, said open end being sized for insertion therethrough of a spool of dental floss,
   a storage area for retaining a quantity of dental flossing material located within said housing,
   material closing said open end of said housing,
   a spool of floss located within said storage area,
   an aperture formed in said housing to permit a strand of floss from said spool to exit said housing, and
   brake means located within said housing to prevent undesired movement of a strand of floss from said spool.

2. The dental floss container of claim 1 wherein:
   said resilient material is a lid.

3. The dental floss container of claim 2 wherein:
   said lid is formed with a skirt encircling said housing and extending substantially the entire length of said housing.

4. The dental floss container of claim 2 wherein:
   said forward end of said housing is stepped inward and said lid is formed with a skirt encircling said forward end of said housing.

5. The dental floss container of claim 2 wherein:
   said brake means is releasable upon depressing of said resilient material.

6. The dental floss container of claim 2 wherein:
   said lid is removably mounted on said housing.

7. The dental floss container of claim 1 wherein:
   said resilient material is a plug.

8. The dental floss container of claim 1 wherein:
   said material is a resilient.

9. The dental floss container of claim 1 further comprising:
   brake means carried by said floss spool, and
   means located in said housing and engageable with said brake means to selectably lock rotation of said floss spool.

10. The dental floss container of claim 9 wherein:
    said brake means is mounted on one end of said floss spool.

11. The dental floss container of claim 10 wherein:
    said floss spool has a central shaft and said brake means is mounted on one end of said shaft.

12. The dental floss container of claim 11 wherein:
    the shaft of said floss spool is cylindrical and said brake means is formed with teeth which are frictionally engageable with mating teeth carried by said resilient means.

13. The dental container of claim 9 wherein:
    said brake means includes flange means having a plurality of teeth, and
    means carried by said housing and engageable with said teeth.

14. The dental floss container of claim 1 further comprising:
    a cutter blade mounted on said housing.

15. The dental floss container of claim 1 wherein:
    said housing is sealable against outside air and moisture.

16. The dental flossing container of claim 1 further comprising:
    means for selectably ventilating said housing.

17. The dental flossing container of claim 1 wherein:
said spool of dental floss is replaceable.
18. The dental flossing container of claim 17 further comprising:
   a cover releasably mountable on said housing to cover said open end of said housing, and
   a cutter blade mounted on said cover.
19. The dental flossing container of claim 1 further comprising:
   a rear cap mounted on said housing,
   vent holes formed in said rear cap and said housing to permit ventilation of said container.
20. The dental flossing container of claim 19 wherein:
said rear cap is movable between a first position in which the vent holes of said rear cap corporate with the vent holes of said container to permit ventilation of said container and a second position in which the vent holes of said rear cap are blocked to prevent air from entering said container.
21. The dental flossing container of claim 1 wherein:
said spool of dental floss can be rewound with new floss upon exhausting of a prior supply.
22. The dental flossing container of claim 1 further comprising:
   a plurality of spools of dental floss interchangeably mountable within said container.
23. The dental flossing container of claim 1 wherein:
said housing is unopenable.
24. The dental flossing container of claim 1 wherein:
said spool of dental floss is replaceably mountable within the dental flossing container of claim 1.
25. The dental flossing container of claim 1 further comprising:
   a lid encircling substantially the entire length of said housing.
26. A dental floss container comprising:
   a cylindrical housing having top and bottom ends and enclosing a storage area,
   a spool of dental floss located within said storage area,
   an aperture formed in said housing to permit a strand of floss from said spool to exit said housing, and
   means for engaging said housing to prevent movement of said strand of floss off of said spool.
27. The dental floss container of claim 26 wherein:
said means is a brake member located within said housing to selectively lock rotation of said spool.
28. A dental floss container comprising:
   a housing having a hollow interior for containing a spool of dental floss, said housing being formed with at least one opening to allow air flow into said interior other than where said floss exits said housing to ventilate said dental floss, and
   means for selectably closing said opening to block said air flow.

* * * * *